United States Patent [19]

Edwards et al.

[11] 4,441,505

[45] Apr. 10, 1984

[54] SENSING DEVICE FOR HUMAN LUNG EXHALATION/INHALATION AIR FLOW MEASUREMENT

[75] Inventors: Raymond A. Edwards; Keith F. Edwards, both of Tuxedo Park, N.Y.

[73] Assignee: Kinetics Measurement Corp., Upper Saddle River, N.J.

[21] Appl. No.: 338,373

[22] Filed: Jan. 11, 1982

[51] Int. Cl.³ .............................................. A61B 5/08
[52] U.S. Cl. .................................. 128/726; 73/861.77
[58] Field of Search .................. 128/725, 726; 272/99; 73/861.77, 861.78, 861.87, 861.88

[56] References Cited

U.S. PATENT DOCUMENTS

| | | | |
|---|---|---|---|
| 2,326,925 | 8/1943 | Bortini | 128/726 |
| 3,230,767 | 1/1966 | Heigl et al. | 73/861.77 |
| 3,680,378 | 8/1972 | Aurilio et al. | 128/726 X |
| 3,814,935 | 6/1974 | Kissel | 73/861.77 |
| 3,949,737 | 4/1976 | Nielsen | 128/726 |
| 4,282,883 | 8/1981 | Yerushalmy | 128/726 |

FOREIGN PATENT DOCUMENTS

| | | | |
|---|---|---|---|
| 1248226 | 8/1967 | Fed. Rep. of Germany | 128/726 |
| 1302375 | 1/1973 | United Kingdom | 128/726 |

*Primary Examiner*—Lee S. Cohen
*Attorney, Agent, or Firm*—Kane, Dalsimer, Kane, Sullivan and Kurucz

[57] ABSTRACT

A spirometer is provided having an air flow path with a housing extending between the ends of a container. A paddle wheel rotor rotates within a cavity and partially cuts across the flow path to define an air gap. The ratio of the cross sectional area of the air gap to the inlet to the flow path is approximately 1:3. A light source/detector is activated by a chopper wheel coaxially mounted with the rotor and adapted to rotate therewith. The detector generates a train of pulses proportional to the rotation of the rotor which in turn is proportional to the volume of air flowing through the air path.

6 Claims, 9 Drawing Figures

SENSING DEVICE FOR HUMAN LUNG EXHALATION/INHALATION AIR FLOW MEASUREMENT

BACKGROUND OF THE INVENTION

The present invention relates to air flow measurement devices and in particular to such devices of the rotor type.

Instruments to measure the ability of a human's lungs to inhale and/or exhale are known as spirometers. Spirometers have heretofore been developed which utilize a rotor for air flow detection and measurement. Such devices are disclosed, for example, in U.S. Pat. Nos. 3,949,737 and 4,034,743 as well as British Pat. No. 1,302,375. The devices disclosed in these references utilize relatively complex mechanisms to convert rotation of the rotor into a measurement of air flow and, as a result, are complex and expensive. In addition, each of these devices fail to take into consideration the fact that the rotor will tend to continue spinning after the air flow cycle has been complete.

In view of the above, it is a principal object of the present invention to provide a relatively simple and inexpensive spirometer of the rotor type.

It is a further object to provide such a spirometer which displays information in a form which may readily be interpreted.

A still further object is to provide such a spirometer which can detect both inhalation and exhalation and which can operate at very low air flows (as when used by an elderly or ill person).

Still another object is to provide such a spirometer which can be used in virtually any environment and which is not effected by humidity in the air flow stream.

Still a further object is to provide such a spirometer which is lightweight, portable and readily and easily utilized with a minimum of training required for its operation.

Still other objects will be apparent from the following description of a preferred embodiment of the invention.

SUMMARY OF THE INVENTION

The above and other beneficial objects and advantages are attained in accordance with the present invention by providing a spirometer comprising a container having top and bottom end caps. A housing is positioned within the chamber secured to the caps in air tight relationship. A flow path extends through the housing terminating at one end in an inlet opening communicating with a mouthpiece stem which extends through the top end cap and at the opposite end in an outlet opening connected to an air screen which extends through the bottom cap. A multi-blade paddle wheel type rotor is positioned in an arcuate cavity in the housing proximal the top end so that its blades rotate in an arc tangential to the flow path. The tips of the rotor blades are spaced apart from the housing wall opposite the cavity so as to define an air gap between the arc described by the rotor blade tips and opposite wall. The rotor blades extend from side to side of the housing sidewalls so that air flowing through the flow path impinges against the rotor blades or flows through the air gap. The ratio of cross-sectional areas of the air gap to inlet opening is approximately 1:3. A light chopper wheel is attached to an extension of the rotor shaft for rotation between a light source and a detector to count rotations of the chopper wheel and hence rotation of the rotor when breath is inhaled or exhaled through a mouthpiece attached to the stem.

The number of rotations of the shaft in a given time period is indicative of the air flow through the path in the time period.

DETAILED DESCRIPTION OF THE PREFERRED EMBODIMENT

Figure 1:
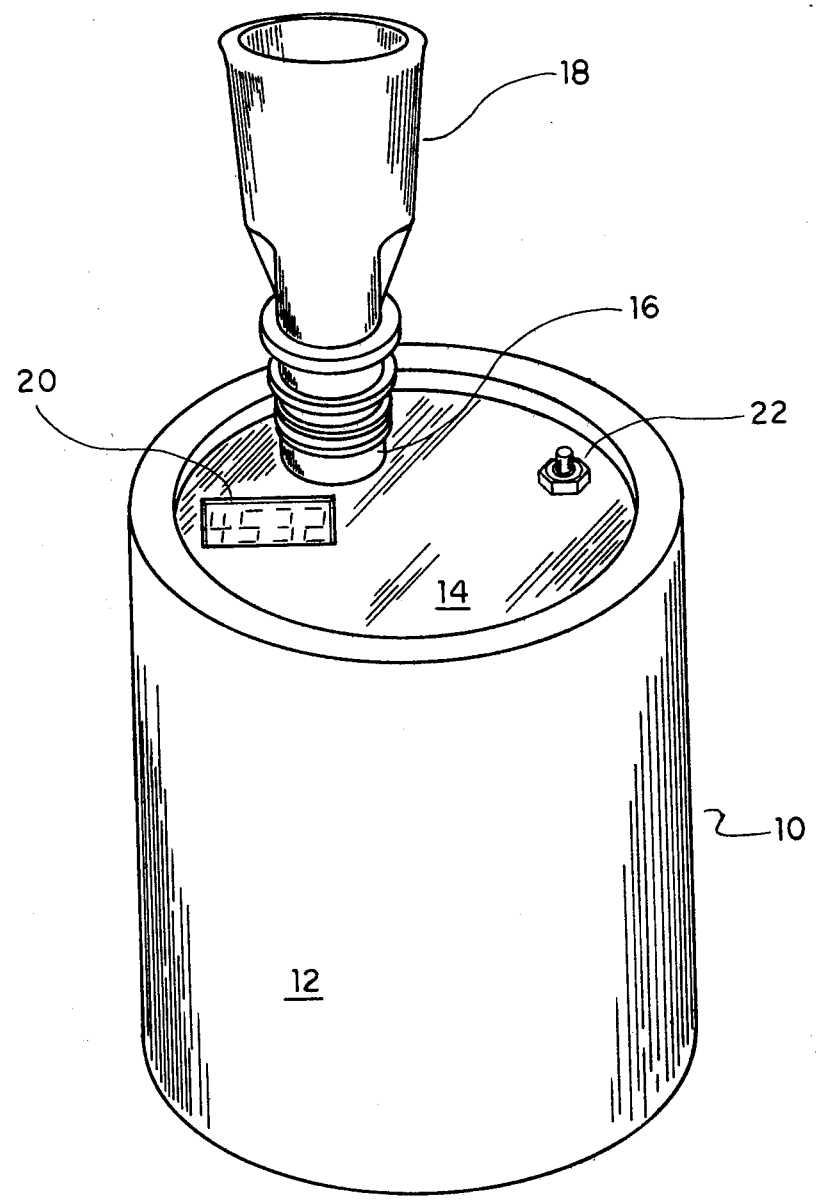
FIG. 1 is a perspective view of a spirometer in accordance with the present invention.

Reference is now made to the drawings and to FIG. 1 in particular wherein a spirometer 10 in accordance with the present invention is depicted. The spirometer 10 comprises an outer container 12 having a top plate 14 through which a mouthpiece stem 16 extends. The stem 16 is adapted to receive a mouthpiece 18 in a simple slip fit. The mouthpiece 18 is preferably replaceable and disposable. A four digit display 20 and control switch 22 are also mounted on the exterior of top plate 14.

Figure 4:
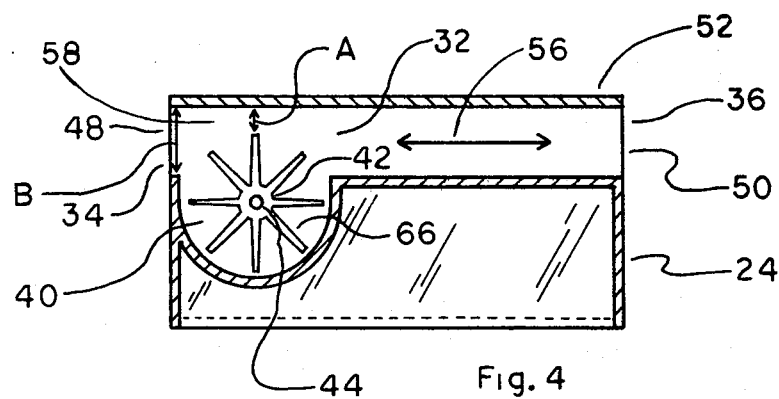
FIG. 4 is a sectional view of the flow housing taken along reference lines 4—4 of FIG. 3 in the direction indicated by the arrows.
Figures 5A, 5B:
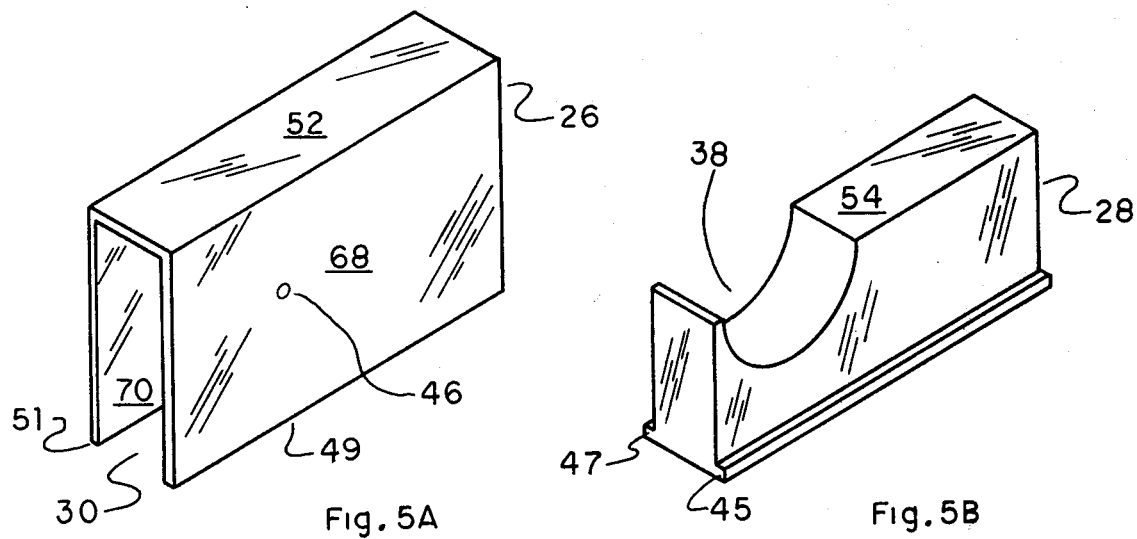
FIGS. 5A and 5B are perspective views of the components from which the flow housing is formed.
Figure 3:
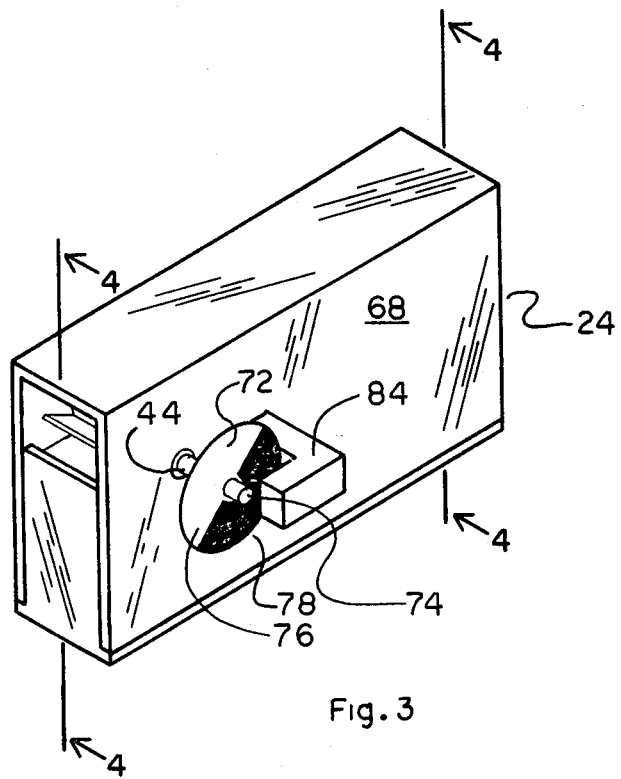
FIG. 3 is a perspective view of the flow housing of the spirometer.

A housing 24 is mounted within container 12 in communication with stem 16. The housing 24 comprises a three-sided member 26 and a cavity member 28 which fits into the open side 30 of the three-sided member 26 closing the same. When fitted together, members 26 and 28 define an air flow path 32 extending between the top end 34 and bottom end 36 of housing 24. As shown in FIGS. 4 and 5B member 28 is formed with an arcuate recess 38 which describes an arc slightly greater than 180°. When the housing 24 is assembled, recess 38 defines an arcuate cavity 40 into which a paddle wheel type rotor 42 coaxially fits. To this end, the rotor 42 is mounted on a shaft 44 which extends through openings 46 in member 26. A pair of flanges 45, 47 on the bottom of member 27 receive the bottom edges 49, 51 of the opposite side walls of member 26 to insure that the openings 46 coaxially align with the center of arcuate cavity 38 when the housing 24 is assembled.

The housing 24 when assembled and positioned within container 12 includes an expired air inlet 48 communicating with stem 16 and an outlet 50. The outer wall 52 of member 26 is common to the inlet and outlet as is the wall 54 of member 28. The inlet 48 and outlet 50 are aligned to define an air path (generally designated 56) which extends tangentially to the arc described by the blades of rotor 42 during rotation.

In order to reduce the pressure drop resulting from friction of the rotor and to compensate for coastdown error the area of the inlet orifice 48 and air gap 58 at the point of tangency are rigidly controlled. To this end the inlet 48 and outlet 50 are located at opposite ends of a chord of the rotor cavity 38.

The ratio of the air gap cross-sectional area (A) to the inlet orifice cross-sectional area (B) is on the order of 1:3. It has been empirically determined that a ratio of 1:2.87 virtually eliminates all error resulting from coastdown of the rotor (i.e., the tendency of the rotor to continue to rotate after the air flow is cut off) to the extent that a substantially linear relationship exists between the number of rotations of the shaft 44 of rotor 42 and the volume of air passing through the air path 56.

The bottom of container 12 is closed by an end plate 60 having a screened air port 62 therein. A battery recharger receptical 64 and on off switch 66 are also mounted on the bottom end plate 60 for the electronics and battery contained within the unit. The top and bottom plates 14, 60 are secured to the opposite ends of housing 24 in a manner so as to prevent air leakage except through the air path 56 of housing 24.

The blades 66 of rotor 42 are identical and each extends radially substantially from shaft 44 to the arcuate surface 38 of member 28. The blades are substantially equally in width to the spacing between the opposed walls 68, 70 of member 26 so that air flowing through the housing impinges on the blades or flows through the air gap. The individual blades are tapered toward their tips thereby reducing the rotational inertia of the assembly.

Figure 2:
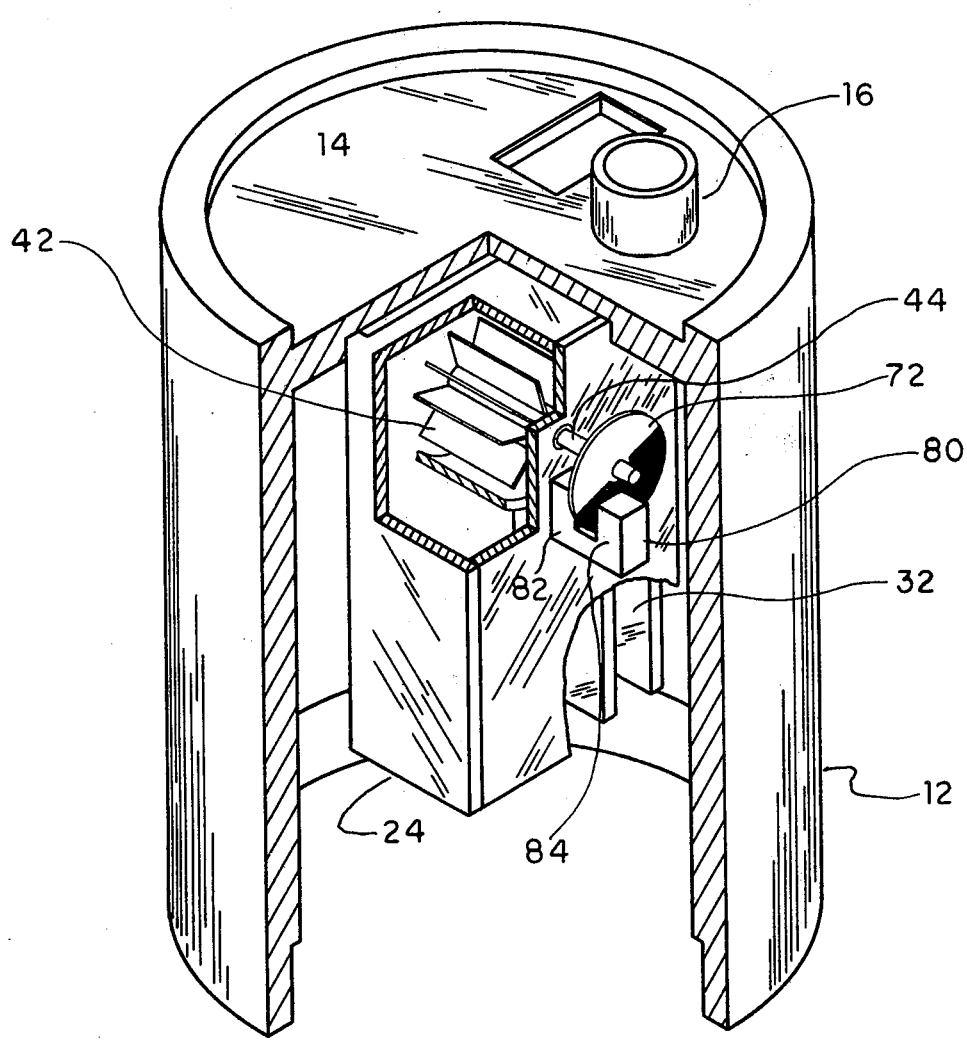
FIG. 2 is a cut-away perspective view of the spirometer with components thereof removed for clarity.
Figure 7:
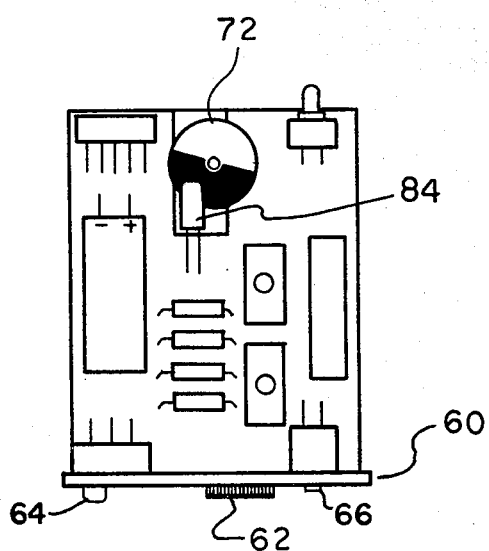
FIG. 7 is a front elevational view of the housing as depicted in FIG. 6.
Figure 6:
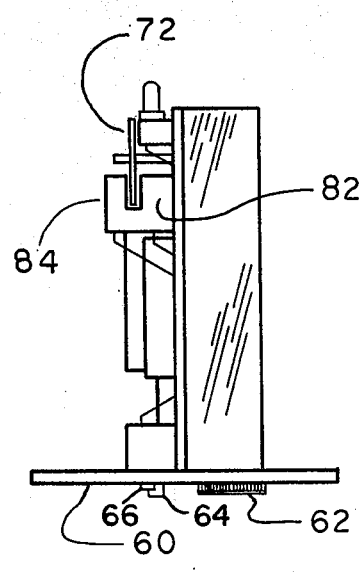
FIG. 6 is an end elevational view of the flow housing with the associated electronics attached and the container bottom end plate in position.
Figure 8:
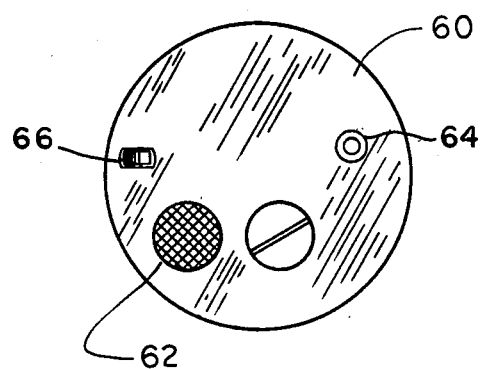
FIG. 8 is a bottom plan view of the spirometer container.

The flow of air through path 32 is detected by means of an optical detector counting the rotations of rotor shaft 46. To this end, a low inertia, light chopping wheel 72 is affixed to an extension 74 of shaft 44. The wheel 72 is divided in half, with one-half 76 transparent to infrared light and the other half 78 opaque to infrared light. The wheel 72 rotates between the legs 82, 84 of U-shaped infrared source-detector 80 (as best seen in FIG. 2). Thus, during each rotation of wheel 72 infrared light is permitted to pass from the light source leg 82 to the light detector leg 84 for half the period of rotation and blocked from passing during the other half of the period of rotation. A counting circuit, the components of which are mounted to the exterior surface 68 of member 26 (as shown in FIGS. 7 and 8) converts the detected light periods into a train of pulses and counts them. The total number of pulses as well as the number of pulses generated over a preselected time (multiplied by a suitable factor) are displayed on display 20.

It should be noted that rotor 72 is free to turn in both directions and thus both inhalation and exhalation will trigger a count which may be displayed.

Thus, in accordance with the above, the aforementioned objects are effectively attained.

Having thus described the invention, what is claimed is:

1. A spirometer comprising:
   a container having a top end cap and a bottom end cap;
   an opening in said top end cap and an opening in said bottom end cap;
   an air flow housing positioned within said container extending between said end caps;
   an air flow path extending longitudinally through said housing, said path terminating at one end in an air inlet communicating with said opening in said top end cap and at the opposite end in an outlet communicating with said opening in said bottom end cap;
   an arcuate cavity in said housing communicating with said flow path and extending transversely thereto;
   a multi-blade paddle wheel type rotor mounted coaxially with said cavity for rotation within said housing with the blades of said rotor extending partially across said flow path;
   an air gap defined between the ends of the blades and the housing, the ratio of the cross-sectional area of said air gap to said inlet being approximately 1:3; and,
   means for counting the rotations of said rotor when air is inhaled or exhaled through said top end cap opening.

2. The invention in accordance with claim 1 wherein said counting means comprises a shaft extending axially through said rotor for rotation therewith; an extension of said shaft extending beyond a sidewall of said housing; a light chopper wheel secured to said extension for rotation therewith; a light source and light detector mounted on opposite sides of said light chopper wheel, means for generating an electrical pulse in response to the output of said light detector, and means for counting said pulses.

3. The invention in accordance with claim 1 further comprising a mouthpiece stem communicating with said top end cap opening and a disposable mouthpiece mounted on said stem.

4. The invention in accordance with claims 1, 2 or 3 wherein said arcuate cavity describes an arc greater than 180°.

5. The invention in accordance with claims 1, 2 or 3 wherein said end caps are parallel to each other and said flow path extends perpendicular to said caps.

6. The invention in accordance with claims 1, 2 or 3 wherein the blades of said rotor are identical and each of said blades tapers as it extends radially outwardly.

* * * * *